United States Patent
Chauhan et al.

(10) Patent No.: US 10,485,812 B2
(45) Date of Patent: Nov. 26, 2019

(54) STABLE ANTIBACTERIAL COMPOSITION

(71) Applicant: WOCKHARDT LIMITED, Aurangabad (IN)

(72) Inventors: Bhaskar Chauhan, Sambhal (IN); Rajendra Nandlal Nagori, Aurangabad (IN); Yatendra Kumar Gupta, Aurangabad (IN)

(73) Assignee: WOCKHARDT LIMITED, Chikalthana, Aurangabad (IN)

( * ) Notice: Subject to any disclaimer, the term of this patent is extended or adjusted under 35 U.S.C. 154(b) by 0 days.

(21) Appl. No.: 15/550,969

(22) PCT Filed: Jan. 11, 2017

(86) PCT No.: PCT/IB2017/050123
§ 371 (c)(1),
(2) Date: Aug. 14, 2017

(87) PCT Pub. No.: WO2017/122127
PCT Pub. Date: Jul. 20, 2017

(65) Prior Publication Data
US 2018/0028549 A1    Feb. 1, 2018

(30) Foreign Application Priority Data
Jan. 12, 2016  (IN) .............................. 201621001034

(51) Int. Cl.
| A61K 31/7048 | (2006.01) |
| A61K 47/18 | (2017.01) |
| A61K 9/19 | (2006.01) |
| A61K 31/194 | (2006.01) |
| A61K 31/198 | (2006.01) |
| A61K 31/455 | (2006.01) |
| A61K 9/00 | (2006.01) |

(52) U.S. Cl.
CPC ........ *A61K 31/7048* (2013.01); *A61K 9/0019* (2013.01); *A61K 9/19* (2013.01); *A61K 31/194* (2013.01); *A61K 31/198* (2013.01); *A61K 31/455* (2013.01); *A61K 47/18* (2013.01)

(58) Field of Classification Search
CPC ...... A61K 9/19; A61K 31/194; A61K 31/198; A61K 31/455; A61K 31/7048; C07H 17/08
See application file for complete search history.

(56) References Cited

FOREIGN PATENT DOCUMENTS

| WO | WO/2007/077219 | 7/2007 |
| WO | WO/2010/136971 | 12/2010 |
| WO | WO/2012/076989 | 6/2012 |
| WO | WO/2012/127351 | 9/2012 |

OTHER PUBLICATIONS

Nireesha, G. et al "Lyophilization/Freeze Drying . . . " Int. J. Novel Trends Pharm. Sci., vol. 3, No. 4, pp. 87-98. (Year: 2013).*
Lee, E. et al "A practical guide to pharmaceutical polymorph . . . " Asian J. Pharm. Sci., vol. 9, pp. 163-174. (Year: 2014).*
Baheti, A. et al "Excipients used in lyophilization . . . " J. Excip. Food Chem., vol. 1, No. 1, pp. 41-54. (Year: 2010).*
Jim O'Neil's publication, 2016. UK government report on antimicrobial resistance (AMR).
Nature Biotechnology vol. 36 No. 7 Jul. 2018, p. 555.
Borst, title: Stability of Five Beta-lactam Antibiotics in Sterile Water for Injection and Stored in Plastic Syringes, Ph.D., dissertation, Jun. 1984.
Kucher—book (3 volumes—Kucers' The Use of Antibiotics: A Clinical Review of Antibacterial, Antifungal, Antiparasitic, and Antiviral Drugs. Published Oct. 2, 2017. A table of contents is filed.
Sivakumar. Isolation and Characterisation of Degradation Impurities in the Cefazolin Sodium Drug Substance—Sci Pharm. 2013; 81: 933-950.

\* cited by examiner

*Primary Examiner* — Leigh C Maier
(74) *Attorney, Agent, or Firm* — Bio Intellectual Property Services (Bio IPS); O. (Sam) Zaghmout

(57) ABSTRACT

The lyophilized solid pharmaceutical compositions comprising a compound of Formula (I) or a stereoisomer or a pharmaceutically acceptable derivative thereof are disclosed.

Formula (I)

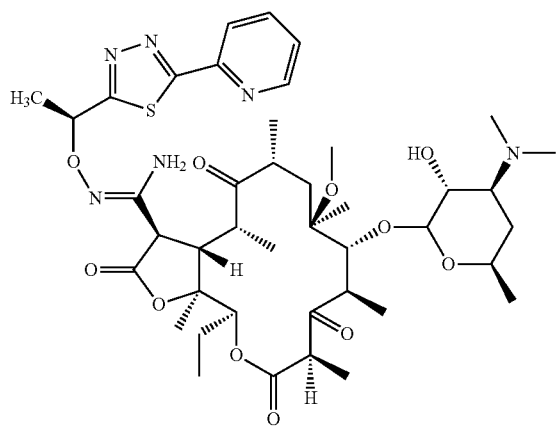

6 Claims, No Drawings

STABLE ANTIBACTERIAL COMPOSITION

PRIORITY APPLICATION(S)

This application claims priority to Indian Patent Application No. 201621001034 filed on Jan. 12, 2016, the disclosures of which is incorporated herein by reference in its entirety as if fully rewritten herein.

FIELD OF THE INVENTION

The invention relates to pharmaceutical compositions comprising an antibacterial agent, a process for preparing such compositions, and use of such compositions in treating bacterial infections.

BACKGROUND OF THE INVENTION

Bacterial infections continue to remain one of the major causes of human diseases. A variety of antibacterial compounds are currently used in treating infections caused by bacteria. PCT International Patent Application Number PCT/IB2011/050464 discloses several compounds having antibacterial activity, including the compound of Formula (I).

Formula (I)

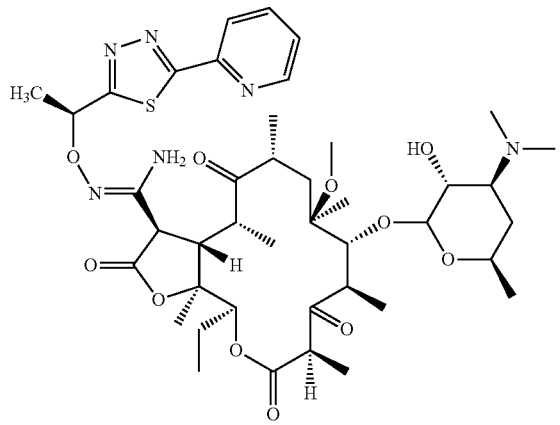

The present invention describes pharmaceutical compositions comprising a compound of Formula (I) or a pharmaceutically acceptable derivative thereof; a process for preparation of such compositions; and use of such compositions in treating bacterial infections.

SUMMARY OF THE INVENTION

Accordingly, there are provided lyophilized solid pharmaceutical compositions comprising a compound of Formula (I) or a stereoisomer or a pharmaceutically acceptable derivative thereof.

Formula (I)

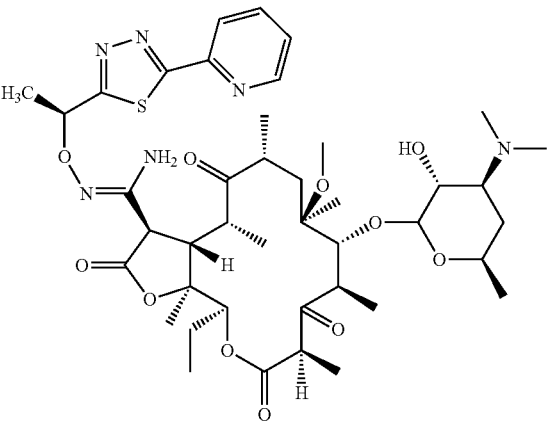

In one general aspect, there are provided lyophilized solid pharmaceutical compositions comprising: (a) a compound of Formula (I) or a stereoisomer or a pharmaceutically acceptable derivative thereof, (b) Niacinamide or a pharmaceutically acceptable derivative thereof, (c) Glycine or a pharmaceutically acceptable derivative thereof, and (d) Citric acid or a pharmaceutically acceptable derivative thereof.

In another general aspect, there is provided a process for preparing a lyophilized solid pharmaceutical composition comprising: (a) a compound of Formula (I) or a stereoisomer or a pharmaceutically acceptable derivative thereof, (b) Niacinamide or a pharmaceutically acceptable derivative thereof, (c) Glycine or a pharmaceutically acceptable derivative thereof, and (d) Citric acid or a pharmaceutically acceptable derivative thereof; said process comprising the steps of: (i) dissolving a compound of Formula (I) or a stereoisomer or a pharmaceutically acceptable derivative thereof, Niacinamide or a pharmaceutically acceptable derivative thereof, Glycine or a pharmaceutically acceptable derivative thereof, and Citric acid or a pharmaceutically acceptable derivative thereof, in an aqueous solvent at a temperature between about 2° C. to about 25° C. to obtain a bulk solution; (ii) adjusting pH of the bulk solution 4-7 (iii) cooling the bulk solution in step (ii) to a temperature below about −20° C. in a lyophilizer; (iv) evacuating the lyophilizer to a pressure of about 400 µbar or less; (v) heating the lyophilizer to about −20° C. or above and maintaining the temperature and pressure for a sufficient time to remove water from the aqueous solvent to form a lyophilized solid; and (vi) drying the lyophilized solid to form a lyophilized composition.

In another general aspect, the compositions according to the invention are used in treating bacterial infections.

In another general aspect, there is provided a method for treating bacterial infection in a subject, said method comprising administering to said subject a therapeutically effective amount of a pharmaceutical composition according to the invention.

The details of one or more embodiments of the invention are set forth in the description below. Other features, objects and advantages of the invention will be apparent from the following description, including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, which would occur to one skilled in the relevant art and having possession of this disclosure, are to be considered within the scope of the invention. It must be noted that, as used in this specification and the appended claims, the singular forms "a", "an", and "the" include plural referents unless the content clearly dictates otherwise. All references including patents, patent applications, and literature cited in the specification are expressly incorporated herein by reference in their entirety.

The invention discloses lyophilized solid pharmaceutical compositions comprising a compound of Formula (I) or a stereoisomer or a pharmaceutically acceptable derivative thereof; a process for preparing such compositions and use of such compositions in treating bacterial infections.

Formula (I)

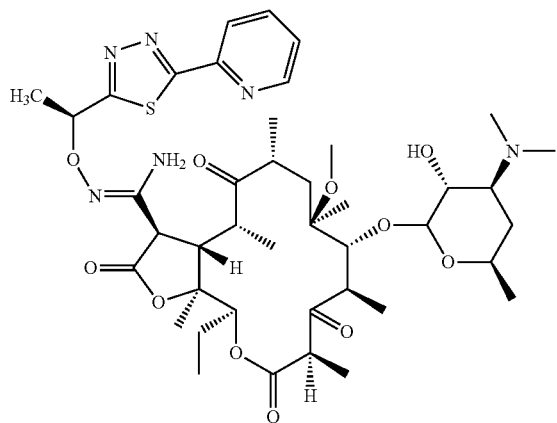

The term "pharmaceutically acceptable derivative" as used herein refers to and includes any pharmaceutically acceptable salt, pro-drugs, metabolites, esters, ethers, hydrates, polymorphs, solvates, complexes and adducts of a compound described herein which, upon administration to a subject, is capable of providing (directly or indirectly) the parent compound. For example, the term "a compound of Formula (I) or a pharmaceutically acceptable derivative thereof" includes all derivatives of the compound of Formula (I) (including pharmaceutically acceptable salts, pro-drugs, metabolites, esters, ethers, hydrates, polymorphs, solvates, complexes and adducts) which, upon administration to a subject, are capable of providing (directly or indirectly) the compound of Formula (I). Likewise, the term "Citric acid or a pharmaceutically acceptable derivative thereof" includes citric acid and all derivatives of citric acid (including pharmaceutically acceptable salts, pro-drugs, metabolites, esters, ethers, hydrates, polymorphs, solvates, complexes and adducts), which upon administration to a subject, are capable of providing (directly or indirectly) citric acid. Typical, non-limiting examples of pharmaceutically acceptable derivatives of citric acid include citric acid monohydrate, sodium citrate di hydrate and a like.

The term "pharmaceutically acceptable salt" as used herein refers to one or more salts of a given compound which possesses the desired pharmacological activity of the free compound and which are neither biologically nor otherwise undesirable. In general, the term "pharmaceutically acceptable salts" refer to salts that are suitable for use in contact with the tissues of human and animals without undue toxicity, irritation, allergic response and the like, and are commensurate with a reasonable benefit/risk ratio. Pharmaceutically acceptable salts are well known in the art. For example, S. M. Berge, et al. (*J. Pharmaceutical Sciences*, 66; 1-19, 1977), incorporated herein by reference in its entirety, describes various pharmaceutically acceptable salts in details. Compound of Formula (I) can be used as such or in the form of its suitable salt. A reference to compound of Formula (I) is intended to include reference to such salts as well.

The term "infection" or "bacterial infection" as used herein includes presence of bacteria, in or on a subject, which, if its growth were inhibited, would result in a benefit to the subject. As such, the term "infection" in addition to referring to the presence of bacteria also refers to presence of normal floras, which are not desirable. The term "infection" includes infection caused by bacteria.

The term "subject" as used herein refers to vertebrate or invertebrate, including a mammal. The term "subject" includes human, animal, a bird, a fish, or an amphibian. Typical, non-limiting examples of a "subject" includes humans, cats, dogs, horses, sheep, bovine cows, pigs, lambs, rats, mice and guinea pigs.

The term "treat", "treating" or "treatment" as used herein refers to administering a medicament, including a pharmaceutical composition, or one or more pharmaceutically active ingredients, for prophylactic and/or therapeutic purposes. The term "prophylactic treatment" refers to treating a subject who is not yet infected, but who is susceptible to, or otherwise is at a risk of infection (preventing the bacterial infection). The term "therapeutic treatment" refers to administering treatment to a subject already suffering from infection. The terms "treat", "treating" or "treatment" as used herein also refer to administering compositions or one or more of pharmaceutically active ingredients discussed herein, with or without additional pharmaceutically active or inert ingredients, in order to: (i) reduce or eliminate either a bacterial infection or one or more symptoms of the bacterial infection, or (ii) retard the progression of a bacterial infection or one or more symptoms of the bacterial infection, or (iii) reduce the severity of a bacterial infection or of one or more symptoms of the bacterial infection, or (iv) suppress the clinical manifestation of a bacterial infection, or (v) suppress the manifestation of adverse symptoms of the bacterial infection.

The term "administration" or "administering" includes delivery of a composition or one or more pharmaceutically active ingredients to a subject, including for example, by any appropriate methods, which serves to deliver the composition or its active ingredients or other pharmaceutically active ingredients to the site of the infection. The method of administration may vary depending on various factors, such as for example, the components of the pharmaceutical composition or the type/nature of the pharmaceutically active or inert ingredients, the site of the potential or actual infection, the microorganism involved, severity of the infection, age and physical condition of the subject and a like. Some non-limiting examples of ways to administer a composition or a pharmaceutically active ingredient to a subject according to this invention include oral, intravenous, topical, intramuscular and parenteral. The compositions according to the invention may also be reconstituted and/or diluted prior to administration.

The compositions according to the invention may further comprise one or more pharmaceutically acceptable excipients. The term "pharmaceutically inert ingredient" or "carrier" or "excipient" refers to a compound or material used to facilitate administration of a compound, for example, to increase the solubility of the compound. Typical, non-limiting examples of solid excipients include, starch, lactose, dicalcium phosphate, sucrose, and kaolin. Typical, non-limiting examples of liquid excipients include sterile water and edible oils such as peanut oil and sesame oil. In addition, various adjuvants commonly used in the art may also be included. These and other such excipients are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press., which is incorporated herein by reference in its entirety.

The term "related substances" as used herein refers to one or more impurities present in the pharmaceutical composition according to the invention. Such impurities may be present in the composition due to degradation of one or more components in the composition, for example the active or inactive ingredients. The amount of impurities is calculated on the basis of the compound of Formula (I) or a pharmaceutically acceptable derivative thereof present in the composition.

The term "N-oxide impurity" as used herein refers to a compound of Formula (II):

Compound of Formula (II)

The term "N-demethyl impurity" as used herein refers to a compound of Formula (III):

Compound of Formula (III)

The term "3-hydroxy impurity" as used herein refers to a compound of Formula (IV):

Compound of Formula (IV)

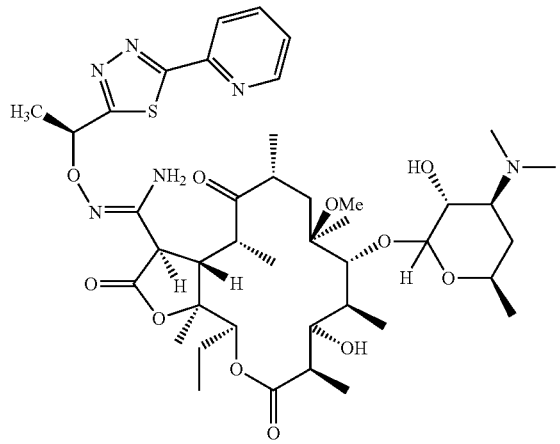

The term "isomer impurity" as used herein refers to a compound of Formula (V):

Compound of Formula (V)

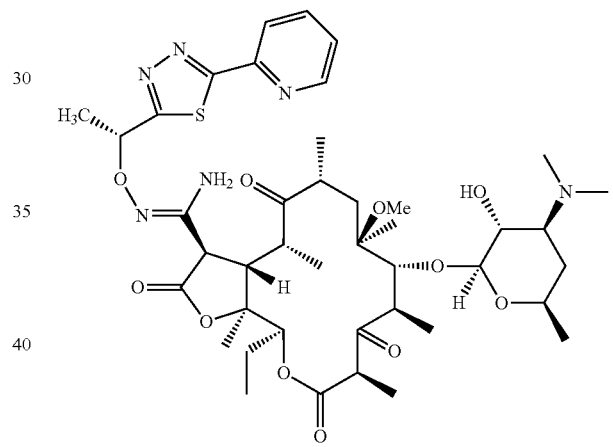

The term "epimer impurity" as used herein refers to a compound of Formula (VI):

Compound of Formula (VI)

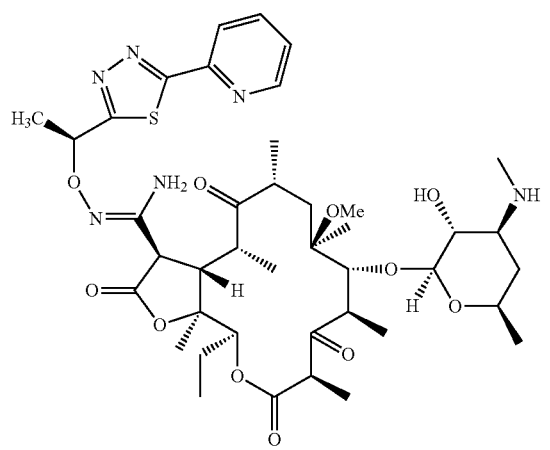

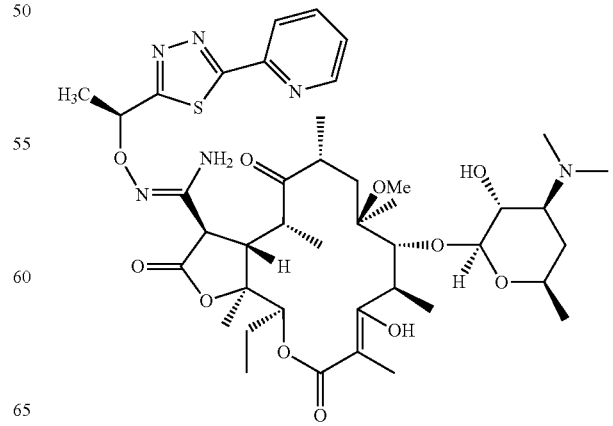

The compositions according to the invention are lyophilized solid pharmaceutical compositions comprising a compound of Formula (I) or a stereoisomer or a pharmaceutically acceptable derivative thereof. The pharmaceutical compositions according to the invention may include one or more pharmaceutically acceptable carriers or excipients or the like. Typical, non-limiting examples of such carriers or excipients include bulking agents, solubilizing agents, stabilizing agents, buffering agents, pH adjusting agents, tonicity adjustors, hydrotropic agent, chelating agents, antioxidants, preservatives and the like.

In some embodiments, the compositions according the invention comprise one or more buffering agents. The presence of buffering agents in the composition enhances overall stability of the composition and controls formation of impurities. In some other embodiments, the type and amount of one or more buffering agents used in the compositions are capable of providing a pH in the range of from about 4 to about 7. Typical, non-limiting examples of buffers include citrate, acetate, phosphate, succinates, tartarate, ascorbate, benzoate, lactates, glutamates, amino acids, gluconate, malate, formate, propionate, carbonate buffer and the like or combinations thereof. In some embodiments, the buffer used in the compositions is a citrate buffer. Typical, non-limiting examples of citrate buffers that can be used in the composition include sodium citrate dihydrate.

In some embodiments, the compositions according to invention comprise one or more organic acid. Typical, non-limiting examples such organic acid include citric acid, acetic acid, hydroxyacetic acid, methanesulphonic acid, tartaric acid, fumaric acid, succinic acid, glutaric acid, adipic acid, propionic acid, ascorbic acid, maleic acid, malic acid, glutamic acid, gluconic acid, glucuronic acid, galacturonic acid and lactic acid and the like or combinations thereof. In some embodiments, the compositions according to the invention comprise citric acid or a pharmaceutically acceptable derivative thereof.

In some other embodiments, the compositions according to invention comprise one or more preservatives. Typical non-limiting examples of preservatives include methylparaben, propylparaben, phenol, benzyl alcohol, benzylalkonium chloride, benzethnium chloride and the like or combinations thereof.

The amount of compound of Formula (I) or a stereoisomer or a pharmaceutically acceptable derivative thereof in the compositions according to the invention can vary depending on various factors, including for example, the age of the subject, nature and extent of infection, desired therapeutic effect etc. In some embodiments, the compositions according to the invention comprise about 10 mg to about 2000 mg of a compound of Formula (I) or a stereoisomer or a pharmaceutically acceptable derivative thereof. In some other embodiments, the composition according to the invention comprises about 100 mg to about 1500 mg of a compound of Formula (I) or a stereoisomer or a pharmaceutically acceptable derivative thereof.

In some embodiments, the compositions according to the invention comprise one or morehydrotropic agents. The term "hydrotropic agent" as used herein refers to includes compounds capable of enhancing solubility of one or more other compounds. Typical, non-limiting examples of hydrotropic agents include glycine, naicinamide, sodium benzoate, sodium ascorbate, sodium citrate or a mixture thereof.

In some embodiments, the compositions according to the invention comprise: (a) a compound of Formula (I) or a stereoisomer or a pharmaceutically acceptable derivative thereof, (b) Niacinamide or a pharmaceutically acceptable derivative thereof, (c) Glycine or a pharmaceutically acceptable derivative thereof, and (d) Citric acid or a pharmaceutically acceptable derivative thereof.

In some other embodiments, the composition according to invention comprises: (a) about 100 mg to about 1500 mg of a compound of Formula (I) or a stereoisomer or a pharmaceutically acceptable derivative thereof, (b) about 100 mg to about 1500 mg of Niacinamide or a pharmaceutically acceptable derivative thereof, (c) about 30 mg to about 600 mg of Glycine or a pharmaceutically acceptable derivative thereof, and (d) about 10 mg to about 300 mg of Citric acid or a pharmaceutically acceptable derivative thereof. However, amounts beyond these ranges can also be employed of desired.

In another aspect, there is also provided a process for preparing a composition comprising: (a) a compound of Formula (I) or a stereoisomer or a pharmaceutically acceptable derivative thereof, (b) Niacinamide or a pharmaceutically acceptable derivative thereof, (c) Glycine or a pharmaceutically acceptable derivative thereof, and (d) Citric acid or a pharmaceutically acceptable derivative thereof; said process comprising the steps of: (i) dissolving a compound of Formula (I) or a stereoisomer or a pharmaceutically acceptable derivative thereof, Niacinamide or a pharmaceutically acceptable derivative thereof, Glycine or a pharmaceutically acceptable derivative thereof, and Citric acid or a pharmaceutically acceptable derivative thereof, in an aqueous solvent at a temperature between about 2° C. to about 25° C. to obtain a bulk solution; (ii) adjusting pH of the bulk solution between 4 to 7; (iii) cooling the bulk solution in step (ii) to a temperature below −20° C. in a lyophilizer, (iv) evacuating the lyophilizer to a pressure of about 400 µbar or less; (v) heating the lyophilizer to about −20° C. or above and maintaining the temperature and pressure for a sufficient time to remove water from the aqueous solvent to form a lyophilized solid; and (vi) drying the lyophilized solid at to form a lyophilized composition. In some embodiments, pH of the bulk solution in step (ii) is adjusted using a buffering agent. In some other embodiments, pH of the bulk solution is adjusted using a citrate buffer. In some embodiments, pH of the bulk solution in step (ii) adjusted using sodium citrate dihydrate, citric acid monohydrate or a mixture thereof. In some embodiments, the bulk solution is obtained by dissolving ingredients at a temperature between about 2° C. to about 40° C., and maintained at this temperature prior to cooling in the lyophilizer. In some other embodiments, the bulk solution is obtained by dissolving ingredients at a temperature between about 2° C. to about 30° C., and maintained at this temperature prior to cooling in the lyophilizer.

In some embodiments, the compositions according to invention are packed in unit dosage amounts into vials, preferably glass vials, under sterile conditions. The vials preferably have capacity sufficient to enable reconstitution of the composition in situ. In some embodiments, the sealed vials are packed in mono cartons.

Any known parenterally acceptable diluent can be used to reconstitute lyophilized powder composition of the invention. In some embodiments, parenterally acceptable diluent comprises water. In some embodiments, water for injection is used as reconstitution diluent. In some other embodiments, an aqueous solution containing a solute such as dextrose or sodium chloride is used for reconstitution. Typical, non-limiting examples of such aqueous solutions include 0.9% sodium chloride injection, 5% dextrose injection, 0.45% sodium chloride injection. In some embodiments, the composition according to invention is reconstituted with a parenterally acceptable diluent, wherein the volume of the diluent is adjusted as per the requirement. In some embodiments, the composition according to invention is reconstituted with 1 ml to 1000 ml of parenterally acceptable diluent. In some embodiments, the composition according to invention is reconstituted with 250 ml to 1000 ml of parenterally acceptable diluent.

In some embodiments, the compositions according to invention are supplied in the form of a kit. A kit may comprise a first container having the lyophilized composition according to invention, and a second container having a compatible reconstitution diluent.

In some embodiments, reconstitutable powder composition according to invention has moisture content of about 0.1% to about 5% by weight.

Advantageously, the compositions according to the invention are stable on storage, as assessed from the impurity content following storage at various conditions.

In some embodiments, the compositions according to the invention comprise less than about 5% w/w of total impurities following one or more of the following:
 (i) storage for three months at a temperature of 40° C. (±2° C.) and a relative humidity of 75% (±5%);
 (ii) storage for six months at a temperature of 40° C. (±2° C.) and a relative humidity of 75% (±5%);
 (iii) storage for three months at a temperature of 25° C. (±2° C.) and a relative humidity of 60% (±5%);
 (iv) storage for six months at a temperature of 25° C. (±2° C.) and a relative humidity of 60% (±5%); or
 (v) storage for six months at a temperature of 30° C. (±2° C.) and a relative humidity of 65% (±5%).

In some other embodiments, the compositions according to the invention comprise about 0.1% w/w to about 5% w/w of total impurities following one or more of the following:
 (i) storage for three months at a temperature of 40° C. (±2° C.) and a relative humidity of 75% (±5%);
 (ii) storage for six months at a temperature of 40° C. (±2° C.) and a relative humidity of 75% (±5%);
 (iii) storage for three months at a temperature of 25° C. (±2° C.) and a relative humidity of 60% (±5%);
 (iv) storage for six months at a temperature of 25° C. (±2° C.) and a relative humidity of 60% (±5%); or
 (v) storage for six months at a temperature of 30° C. (±2° C.) and a relative humidity of 65% (±5%).

In some embodiments, the compositions according to the invention comprise less than about 5% w/w of epimer impurity following one or more of the following:
 (i) storage for three months at a temperature of 40° C. (±2° C.) and a relative humidity of 75% (±5%);
 (ii) storage for six months at a temperature of 40° C. (±2° C.) and a relative humidity of 75% (±5%);
 (iii) storage for three months at a temperature of 25° C. (±2° C.) and a relative humidity of 60% (±5%);
 (iv) storage for six months at a temperature of 25° C. (±2° C.) and a relative humidity of 60% (±5%); or
 (v) storage for six months at a temperature of 30° C. (±2° C.) and a relative humidity of 65% (±5%).

In some embodiments, the compositions according to the invention comprise about 0.1% w/w to about 5% w/w of epimer impurity following one or more of the following:
 (i) storage for three months at a temperature of 40° C. (±2° C.) and a relative humidity of 75% (±5%);
 (ii) storage for six months at a temperature of 40° C. (±2° C.) and a relative humidity of 75% (±5%);
 (iii) storage for three months at a temperature of 25° C. (±2° C.) and a relative humidity of 60% (±5%);
 (iv) storage for six months at a temperature of 25° C. (±2° C.) and a relative humidity of 60% (±5%); or
 (v) storage for six months at a temperature of 30° C. (±2° C.) and a relative humidity of 65% (±5%).

In some embodiments, the compositions according to the invention comprise less than about 5% w/w of moisture following one or more of the following:
 (i) storage for three months at a temperature of 40° C. (±2° C.) and a relative humidity of 75% (±5%);
 (ii) storage for six months at a temperature of 40° C. (±2° C.) and a relative humidity of 75% (±5%);
 (iii) storage for three months at a temperature of 25° C. (±2° C.) and a relative humidity of 60% (±5%);
 (iv) storage for six months at a temperature of 25° C. (±2° C.) and a relative humidity of 60% (±5%); or
 (v) storage for six months at a temperature of 30° C. (±2° C.) and a relative humidity of 65% (±5%).

In some embodiments, the compositions according to the invention comprise about 0.1% w/w to about 5% w/w of moisture following one or more of the following:
 (i) storage for three months at a temperature of 40° C. (±2° C.) and a relative humidity of 75% (±5%);
 (ii) storage for six months at a temperature of 40° C. (±2° C.) and a relative humidity of 75% (±5%);
 (iii) storage for three months at a temperature of 25° C. (±2° C.) and a relative humidity of 60% (±5%);
 (iv) storage for six months at a temperature of 25° C. (±2° C.) and a relative humidity of 60% (±5%); or
 (v) storage for six months at a temperature of 30° C. (±2° C.) and a relative humidity of 65% (±5%).

In some other embodiments, the compositions according to the invention comprise less than about 1% w/w of N-oxide impurity following one or more of the following:
 (i) storage for three months at a temperature of 40° C. (±2° C.) and a relative humidity of 75% (±5%);
 (ii) storage for six months at a temperature of 40° C. (±2° C.) and a relative humidity of 75% (±5%);
 (iii) storage for three months at a temperature of 25° C. (±2° C.) and a relative humidity of 60% (±5%);
 (iv) storage for six months at a temperature of 25° C. (±2° C.) and a relative humidity of 60% (±5%); or
 (v) storage for six months at a temperature of 30° C. (±2° C.) and a relative humidity of 65% (±5%).

In some embodiments, the compositions according to the invention comprise about 0.01% w/w to about 1% w/w of N-oxide impurity following one or more of the following:
 (i) storage for three months at a temperature of 40° C. (±2° C.) and a relative humidity of 75% (±5%);
 (ii) storage for six months at a temperature of 40° C. (±2° C.) and a relative humidity of 75% (±5%);
 (iii) storage for three months at a temperature of 25° C. (±2° C.) and a relative humidity of 60% (±5%);
 (iv) storage for six months at a temperature of 25° C. (±2° C.) and a relative humidity of 60% (±5%); or
 (v) storage for six months at a temperature of 30° C. (±2° C.) and a relative humidity of 65% (±5%).

In some other embodiments, the compositions according to the invention comprise less than about 1% w/w of N-demethyl impurity following one or more of the following:
 (i) storage for three months at a temperature of 40° C. (±2° C.) and a relative humidity of 75% (±5%);
 (ii) storage for six months at a temperature of 40° C. (±2° C.) and a relative humidity of 75% (±5%);
 (iii) storage for three months at a temperature of 25° C. (±2° C.) and a relative humidity of 60% (±5%);

(iv) storage for six months at a temperature of 25° C. (±2° C.) and a relative humidity of 60% (±5%); or (v) storage for six months at a temperature of 30° C. (±2° C.) and a relative humidity of 65% (±5%).

In some embodiments, the compositions according to the invention comprise about 0.01% w/w to about 1% w/w of N-demethyl impurity following one or more of the following:

(i) storage for three months at a temperature of 40° C. (±2° C.) and a relative humidity of 75% (±5%);

(ii) storage for six months at a temperature of 40° C. (±2° C.) and a relative humidity of 75% (±5%);

(iii) storage for three months at a temperature of 25° C. (±2° C.) and a relative humidity of 60% (±5%);

(iv) storage for six months at a temperature of 25° C. (±2° C.) and a relative humidity of 60% (±5%); or (v) storage for six months at a temperature of 30° C. (±2° C.) and a relative humidity of 65% (±5%).

In some embodiments, the compositions according to the invention comprise less than about 1% w/w of 3-hydroxy impurity following one or more of the following:

(i) storage for three months at a temperature of 40° C. (±2° C.) and a relative humidity of 75% (±5%);

(ii) storage for six months at a temperature of 40° C. (±2° C.) and a relative humidity of 75% (±5%);

(iii) storage for three months at a temperature of 25° C. (±2° C.) and a relative humidity of 60% (±5%);

(iv) storage for six months at a temperature of 25° C. (±2° C.) and a relative humidity of 60% (±5%); or (v) storage for six months at a temperature of 30° C. (±2° C.) and a relative humidity of 65% (±5%).

In some other embodiments, the compositions according to the invention comprise about 0.01% w/w to about 1% w/w of 3-hydroxy impurity following one or more of the following:

(i) storage for three months at a temperature of 40° C. (±2° C.) and a relative humidity of 75% (±5%);

(ii) storage for six months at a temperature of 40° C. (±2° C.) and a relative humidity of 75% (±5%);

(iii) storage for three months at a temperature of 25° C. (±2° C.) and a relative humidity of 60% (±5%);

(iv) storage for six months at a temperature of 25° C. (±2° C.) and a relative humidity of 60% (±5%); or (v) storage for six months at a temperature of 30° C. (±2° C.) and a relative humidity of 65% (±5%).

In some embodiments, the compositions according to the invention comprise less than about 1% w/w of the isomer impurity following one or more of the following:

(i) storage for three months at a temperature of 40° C. (±2° C.) and a relative humidity of 75% (±5%);

(ii) storage for six months at a temperature of 40° C. (±2° C.) and a relative humidity of 75% (±5%);

(iii) storage for three months at a temperature of 25° C. (±2° C.) and a relative humidity of 60% (±5%);

(iv) storage for six months at a temperature of 25° C. (±2° C.) and a relative humidity of 60% (±5%); or (v) storage for six months at a temperature of 30° C. (±2° C.) and a relative humidity of 65% (±5%).

In some embodiments, the compositions according to the invention comprise about 0.01% w/w to about 1% w/w of isomer impurity following one or more of the following:

(i) storage for three months at a temperature of 40° C. (±2° C.) and a relative humidity of 75% (±5%);

(ii) storage for six months at a temperature of 40° C. (±2° C.) and a relative humidity of 75% (±5%);

(iii) storage for three months at a temperature of 25° C. (±2° C.) and a relative humidity of 60% (±5%);

(iv) storage for six months at a temperature of 25° C. (±2° C.) and a relative humidity of 60% (±5%); or (v) storage for six months at a temperature of 30° C. (±2° C.) and a relative humidity of 65% (±5%).

The compositions according to the invention are useful treating a variety of bacterial infections. Typical, non-limiting examples of infections that can be treated using the compositions according to the invention include those resulting in pneumonia, otitis media, sinusitus, bronchitis, tonsillitis, mastoiditis, pharynigitis, rheumatic fever, glomerulonephritis, respiratory tract infections, skin and soft tissue infections, abscesses and osteomyelitis, puerperal fever, urinary tract infections, urethritis, cervicitis, sexually transmitted diseases, toxin diseases, ulcers, systemic febrile syndromes, Lyme disease, conjunctivitis, keratitis, dacrocystitis, disseminated *Mycobacterium avium* complex (MAC) disease, gastroenteritis, intestinal protozoa related to infections, odontogenic infections, cough related to infection, gas gangrene related to infection, and atherosclerosis related to infection.

Typical, non-limiting examples of infections in animals that can be treated using compositions according to the invention include bovine respiratory diseases related to infection by *Mannheimia haemolytica*, *Pasteurella multocida*, *Histophilus somni*, *Mycoplasma bovis* or *Bordetella* spp.; cow enteric disease related to infection by *Escherichia coli* or protozoa (i.e., coccidia, cryptosporidia, etc.); dairy cow mastitis related to infection by *Staphylococcus aureus*, *Streptococcus uberis*, *Streptococcus agalactiae*, *Streptococcus dysgalactiae*, *Klebsiella* spp., *Corynebacterium*, or *Enterococcus* spp.; swine respiratory disease related to infection by *Actinobacillus pleuropneumonia*, *Pasteurella multocida*, or *Mycoplasma* spp.; swine enteric disease related to infection by *E. coli*, *Lawsonia intracellularis*, *Salmonella*, or *Serpulinahyodyisinteriae*; cow footrot related to infection by *Fusobacterium* spp.; cow metritis related to infection by *Escherichia coli*; cow hairy warts related to infection by *Fusobacterium necrophorum* or *Bacteroides nodosus*; cow pink-eye related to infection by *Moraxella bovis*; cow premature abortion related to infection by protozoa (i.e. neosporium); urinary tract infection in dogs and cats related to infection by *Escherichia coli*; skin and soft tissue infections in dogs and cats related to infection by *Staphylococcus epidermidis*, *Staphylococcus intermedius*, Coagulase negative *Staphylococci* or *Pasteurella multocida*; and dental or mouth infections in dogs and cats related to infection by *Alcaligenes* spp., *Bacteroides* spp., *Clostridium* spp., *Enterobacter* spp., *Eubacterium*, *Peptostreptococcus*, *Porphyromonas*, or *Prevotella*.

In general, the compositions according to the invention are useful in treating infections caused by various microorganisms. In some embodiments, compositions according to the invention are useful in treating infections caused by *Staphylococcus* spp., *Streptococcus* spp., *Haemophilus* spp., *Moracella* spp., *Legionella* spp., *Chlamydia* spp., *Clostridium* spp. or *Mycoplasma* spp. Typical, non-limiting examples of *Staphylococcus* spp. include *Staphylococcus aureus*, *Staphylococcus epedermidis*, *Staphylococcus saprophyticus* and the like. Typical, non-limiting examples of *Streptococcus* spp. include *Streptococcus agalactiae*, *Streptococcus anginosus*, *Streptococcus bovis*, *Streptococcus canis*, *Streptococcus constellatus*, *Streptococcus dysgalactiae*, *Streptococcus equinus*, *Streptococcus iniae*, *Streptococcus intermedius*, *Streptococcus milleri*, *Streptococcus mitis*, *Streptococcus mutans*, *Streptococcus oxalis*, *Streptococcus parasanguinis*, *Streptococcus peroris*, *Streptococcus pneumoniae*, *Streptococcus pseudopneumoniae*, *Streptococcus pyogenes, Streptococcus ratti, Streptococcus salivarius, Streptococcus tigurinus, Streptococcus thermophilus, Streptococcus sanguinis, Streptococcus sobrinus, Streptococcus suis, Streptococcus uberis, Streptococcus vestibularis, Streptococcus zooepidemicus, Groups C and G streptococci, Viridans streptococci, Groups A, B, and C streptococci, Streptococcal groups C-F (minute-colony streptococci), and the like. Typical, non-limiting examples of Haemophilus spp. include Haemophilus aegyptius, Haemophilus aphrophilus, Haemophilus avium, Haemophilus ducreyi, Haemophilus felis, Haemophilus haemolyticus, Haemophilus influenzae, Haemophilus parainfluenzae, Haemophilus paracuniculus, Haemophilus parahaemolyticus, Haemophilus pittmaniae, Haemophilus segnis, Haemophilus somnus and the like. Typical, non-limiting examples of Moracella spp. include Moracella atlantae, Moracella boevrei, Moracella bovis, Moracella bovoculi, Moracella canis, Moracella caprae, Moracella catarrhalis, Moracella caviae, Moracella cuniculi, Moracella equi, Moracella lacunata, Moracella lincolnii, Moracella nonliquefaciens, Moracella oblonga, Moracella osloensis, Moracella pluranimalium, Moracella porci and the like. Typical, non-limiting example of Legionella spp. include Legionella adelaidensis, Legionella anisa, Legionella beliardensis, Legionella birminghamensis, Legionella bozemanae, Legionella brunensis, Legionella busanensis, Legionella cardiaca, Legionella cherrii, Legionella cincinnatiensis, Legionella donaldsonii, Legionella drancourtii, Legionella dresdenensis, Legionella drozanskii, Legionella dumoffii, Legionella erythra, Legionella fairfieldensis, Legionella fallonii, Legionella feeleii, Legionella geestiana, Legionella gormanii, Legionella gratiana, Legionella gresilensis, Legionella hackeliae, Legionella impletisoli, Legionella israelensis, Legionella jamestowniensis, Legionella jeonii, Legionella jordanis, Legionella lansingensis, Legionella londiniensis, Legionella longbeachae, Legionella lytica, Legionella maceachernii, Legionella massiliensis, Legionella micdadei, Legionella monrovica, Legionella moravica, Legionella nagasakiensis, Legionella nautarum, Legionella oakridgensis, Legionella parisiensis, Legionella pittsburghensis, Legionella pneumophila, Legionella quateirensis, Legionella quinlivanii, Legionella rowbothamii, Legionella rubrilucens, Legionella sainthelensi, Legionella santicrucis, Legionella shakespearei, Legionella spiritensis, Legionella steelei, Legionella steigerwaltii, Legionella taurinensis, Legionella tucsonensis, Legionella tunisiensis, Legionella wadsworthii, Legionella waltersii, Legionella worsleiensis, Legionella yabuuchiae and the like. Typical non-limiting examples of Chlamydia spp. include Chlamydia muridarum, Chlamydia philapecorum, Chlamydia suis, Chlamydia trachomatis, Chlamydia pneumoniae and the like. Typical non-limiting examples of Clostridium spp. include Clostridium diptheriae, Clostridium perfringens and the like. Typical non-limiting examples of Mycoplasma spp. include Mycoplasma amphoriforme, Mycoplasma buccale, Mycoplasma faucium, Mycoplasma fermentans, Mycoplasma genitalium, Mycoplasma hominis, Mycoplasma lipophilum, Mycoplasma orale, Mycoplasma penetrans, Mycoplasma pirum, Mycoplasma pneumoniae, Mycoplasma primatum, Mycoplasma salivarium, Mycoplasma spermatophilum and the like.

In some embodiments, compositions according to the invention are useful in treating infections caused by Peptostreptococcus spp., Actinobacillus haemolyticum, Mycoplasma pneumoniae, Corynebacterium minutissimum, Bartonella henselae; Enterococcus spp., Treponema pallidum, Ureaplasma urealyticum, Neiserria gonorrheae; Helicobacter pylori; Borrelia recurrentis; Borrelia burgdorferi; Listeria spp., Mycobacterium avium complex (MAC) Mycobacterium avium, Mycobacterium intracellulare, Campylobacter jejuni; Cryptosporidium spp.; Bordetella pertussis; Bacteroides spp. and the like.

In some embodiments, there is also provided a method for treating bacterial infection in a subject, said method comprising administering to said subject a therapeutically effective amount of a pharmaceutical composition according to invention.

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compositions, methods and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

Typical batch of a composition according to the invention was prepared as follows. A compound of Formula (I) (5600 gm), Niacinamide USP (5600 gm), Glycine USP (2100 gm), and Citric acid monohydrate USP (840 gm) were weighed. About 77 L of Water for Injection was separately dispensed in a jacketed stainless steel manufacturing vessel, purged with nitrogen and maintained at a temperature 2-8° C. A weighed quantity of citric acid monohydrate was dissolved in about 35 L of the water for injection dispensed earlier to obtain a clear solution. To this solution, a weighed quantity of Niacinamide was and stirred to obtain a clear solution. To this solution, a weighed quantity of a compound of Formula (I) was added under stirring to obtain a clear solution. To this solution, a weighed quantity of Glycine was added to obtain a clear solution. Adjust the pH of the bulk solution so obtained to about 5 to 6 with the help of sodium citrate dihydrate solution. Use citric acid monohydrate solution if required. Make up the volume of the bulk solution to 70 L with Water for Injection. Keep the bulk solution at a temperature between 2° C. to 8° C. throughout. Filter the bulk solution using a PVDF filter. Fill the appropriate amount of bulk solution into 10 mL clear glass vials and initiate partial stoppering with 20 mm Chlorobutyl rubber stopper after flushing with nitrogen. Load partially stoppered filled vials in pre-cooled shelves (5° C.) and start Lyophilisation cycle. In a typical lyophilisation cycle, the lyophiliser containing partially filled vials is cooled to a temperature below −20° C. and maintained at the temperature for desired time, and then the lyophiliser is evacuated to a pressure of about 400 μbar or less and held at that vacuum for a set time. The lyophiliser is then heated to a temperature of about −20° C. or above and the temperature and pressure is maintained for a sufficient time to remove water from the aqueous solvent to form a lyophilized solid in the vials. The vials are then sealed with 20 mm aluminium flip of seals.

Typically, vials were filled in such a way that the each vial contains a lyophilized composition as per details in Table 1.

TABLE 1

Typical details of the composition in a vial as per Example 1

| Sr. | Ingredients | mg/vial |
|---|---|---|
| 1. | Compound of Formula (I) | 400.00 |
| 2. | Niacinamide | 400.00 |
| 3. | Glycine | 150.00 |
| 4. | Citric acid monohydrate | 60.00 |
| 5. | Citric acid monohydrate/Tri sodium citrate dehydrate | Quantity sufficient for pH adjustment |

The composition prepared according to Example 1 was investigated for stability at accelerated conditions of temperature and relative humidity. The Table 2 summarize the results of stability testing at different conditions of relative humidity and temperature.

The invention claimed is:

1. A lyophilized solid pharmaceutical composition comprising: (a) a compound of Formula (I):

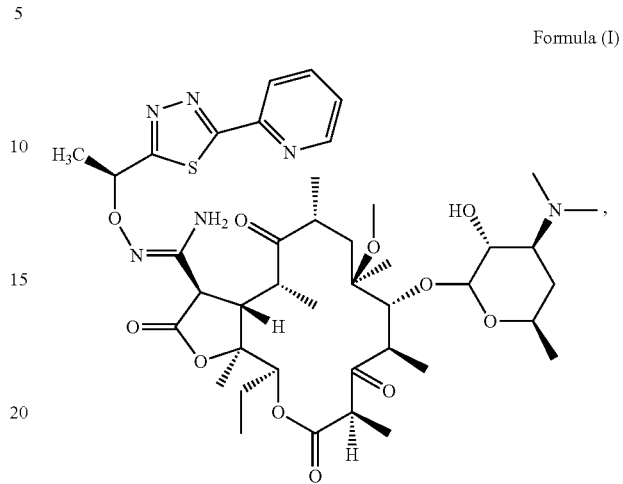

Formula (I)

or a stereoisomer or a pharmaceutically acceptable salt thereof, (b) Niacinamide or a pharmaceutically acceptable salt thereof, (c) Glycine or a pharmaceutically acceptable salt thereof, and (d) Citric acid or a pharmaceutically acceptable salt thereof wherein said composition is stable during storage.

2. The composition according to claim 1, comprising: (a) about 100 mg to about 1500 mg of a compound of Formula (I) or a stereoisomer or a pharmaceutically acceptable salt thereof, (b) about 100 mg to about 1500 mg of Niacinamide or a pharmaceutically acceptable salt thereof, (c) about 30

TABLE 3

Stability study of compositions according to invention at pH 5.5 ± 0.2

| | Tests | Initial | 40° C. ± 2° C./ 75% ± 5% Relative Humidity | | | 25° C. ± 2° C./ 60% ± 5% Relative Humidity | | 30° C. ± 2° C./ 65% ± 5% Relative Humidity | 2-8° C. |
|---|---|---|---|---|---|---|---|---|---|
| | | | 1 Month | 3 Month | 6 Month | 3 Month | 6 Month | 6 Month | 6 Month |
| Description | Lyophilized Vial | White colored lyophilized cake | White colored lyophilized cake | White colored lyophilized cake | White colored lyophilized cake | White colored lyophilized cake | White colored lyophilized cake | White colored lyophilized cake | White colored lyophilized cake |
| | After reconstitution with 5 ml water for injection | Clear colorless to pale colored solution | Clear colorless to pale colored solution | Clear colorless to pale colored solution | Clear colorless to pale colored solution | Clear colorless to pale colored solution | Clear colorless to pale colored solution | Clear colorless to pale colored solution | Clear colorless to pale colored solution |
| Water content (%) | | 0.78 | 0.95 | 0.88 | 0.88 | 0.98 | 0.69 | 0.76 | 0.63 |
| Osmolality (mOsm/kg) | | 351 | 347 | 352 | 355 | 349 | 352 | 355 | 352 |
| pH (after Reconstitution) | | 5.39 | 5.35 | 5.30 | 5.32 | 5.32 | 5.36 | 5.32 | 5.36 |
| Related Substance | | | | | | | | | |
| N-oxide Impurity | | 0.000 | 0.00 | 0.052 | 0.079 | 0.023 | 0.041 | 0.060 | 0.000 |
| N-demethyl Impurity | | 0.096 | 0.079 | 0.132 | 0.153 | 0.113 | 0.122 | 0.139 | 0.089 |
| 3-Hydroxy Impurity | | 0.167 | 0.152 | 0.145 | 0.143 | 0.142 | 0.144 | 0.143 | 0.146 |
| Isomer Impurity | | 0.153 | 0.117 | 0.086 | 0.075 | 0.094 | 0.080 | 0.078 | 0.081 |
| Epimer Impurity | | 3.068 | 3.174 | 3.431 | 3.308 | 2.759 | 2.736 | 2.881 | 2.654 |
| Highest Unknown Impurity | | 0.072 | 0.085 | 0.066 | 0.064 | 0.063 | 0.061 | 0.062 | 0.062 |
| Total Unknown Impurities | | 0.285 | 0.321 | — | — | — | — | — | — |
| Total Impurities | | 3.769 | 3.843 | 4.198 | 4.021 | 3.399 | 3.297 | 3.512 | 3.146 |
| Assay of Compound of Formula (I) (%) | | 108.3 | 108.2 | 104.9 | 106.5 | 107.4 | 107.0 | 107.5 | 106.2 | mg to about 600 mg of Glycine or a pharmaceutically acceptable salt thereof, and (d) about 10 mg to about 300 mg of Citric acid or a pharmaceutically acceptable salt thereof.

3. A process for preparing a composition according to claim 1, said process comprising the steps of: (i) dissolving a compound of Formula (I) or a stereoisomer or a pharmaceutically acceptable salt thereof, Niacinamide or a pharmaceutically acceptable salt thereof, Glycine or a pharmaceutically acceptable salt thereof, and Citric acid or a pharmaceutically acceptable salt thereof, in an aqueous solvent to obtain a bulk solution; (ii) adjusting the pH of the bulk solution between 4 to 7; (iii) cooling the bulk solution in step (ii) to a temperature below −20 ° C. in a lyophilizer, (iv) evacuating the lyophilizer to a pressure of about 400 μbar or less; (v) heating the lyophilizer to about −20 ° C. or above and maintaining the temperature and pressure for a sufficient time to remove water from the aqueous solvent to form a lyophilized solid; and (vi) drying the lyophilized solid to form a lyophilized composition.

4. The process according to claim 3, wherein the pH of the bulk solution in step (ii) is adjusted using a citrate buffer.

5. A composition obtainable by the process according to claim 3.

6. A composition obtainable by the process according to claim 4.

\* \* \* \* \*